United States Patent [19]
Chang et al.

[11] Patent Number: 5,627,640
[45] Date of Patent: May 6, 1997

[54] METHOD FOR MEASURING RADICAL SPECIES DISTRIBUTION IN PLASMA AND AN APPARATUS THEREFOR

[75] Inventors: Hong-Young Chang, Taejon; Pyung-Woo Lee, Kyonggi-do; Yong-Jin Kim, Seoul, all of Rep. of Korea

[73] Assignee: Korea Advanced Institute of Science and Technology, Taejon, Rep. of Korea

[21] Appl. No.: 588,308

[22] Filed: Jan. 18, 1996

[30] Foreign Application Priority Data

Jan. 20, 1995 [KR] Rep. of Korea .......................... 95-945

[51] Int. Cl.[6] .................................................. G01J 3/30
[52] U.S. Cl. ........................................................ 356/316
[58] Field of Search .............................. 356/72, 381, 382, 356/369, 368, 366, 364, 316; 156/626.1; 250/225; 324/71.1

[56] References Cited

PUBLICATIONS

Lee, P.W. et al., "In Situ Monitoring of the Relative Distribution of Radicals by a Two Probes System", Rev. Sci. Instrum., 66(9), pp. 4591–4594, (Sep. 1995).

Rogoff, G. L., "Optical System for Spatial Discrimination of Radiation from Extended Bodies", Applied Optics, 8(3), pp. 723–724 (Mar. 1969).

*Primary Examiner*—K. Hantis
*Attorney, Agent, or Firm*—Oblon, Spivak, McClelland, Maier & Neustadt, P.C.

[57] ABSTRACT

The present invention relates to a method for measuring radical species distribution in plasma by determining the intensity of the light emitted from the radical species and plasma parameters in plasma with the aid of optical and electrostatic probes, and an apparatus for measuring the radical species distribution. The method of the invention comprises the steps of: (i) measuring integral light intensity in a vacuum container by an optical probe inserted to the vacuum container; (ii) determining light intensity at each point of the vacuum container by differentiating the integral light intensity; (iii) measuring current and voltage applied to the electrostatic probe in the vacuum container; (iv) determining plasma parameters from the measured current and voltage; and, (v) measuring distribution of radical species from the light intensity and plasma parameters.

7 Claims, 2 Drawing Sheets

31  32  33  34

41  42

4  3  51

METHOD FOR MEASURING RADICAL SPECIES DISTRIBUTION IN PLASMA AND AN APPARATUS THEREFOR

FIELD OF THE INVENTION

The present invention relates to a method for measuring radical species distribution in plasma and an apparatus therefor, more specifically, to a method for measuring radical species distribution in plasma by determining the intensity of the light emitted from the radical species and plasma parameters in plasma with the aid of optical and electrostatic probes, and an apparatus for measuring the radical species distribution.

BACKGROUND OF THE INVENTION

Plasma is made up of neutral gas, electron and ion. The neutral gas in plasma is activated by collision with the electron and ion to produce radical species(hereinafter referred to as "radicals"), which in turn emits light with a specific wavelength, mainly belonging to a radio-frequency wave or micro-wave. In the microelectronic industry, radicals have been known to play an important role for etching and deposition of thin films; and, therefore, studies on the spatial uniformity of the radicals have been actively carried out. In particular, since the spatial uniformity in a vacuum container used in the formation of plasma is crucial in good performance in the etching and deposition processes, there exists a continuous need to develop a method by which the radical distribution in plasma is measurable in an efficient and precise manner.

On the other hand, the actinometry employed in the etching process of thin films in the microelectronic industry, has been used for measuring the radicals in plasma. According to the actinometry, under a state that a small quantity of an inert gas called as an actinometer is added to such a reactive gas as $SF_6$, $CF_4$, $Cl_2$, $O_2$ and the like, distribution of radicals such as fluoride, chloride and oxide is measured by analyzing the intensity of the light emitted from the radicals and the actinometer. The aforementioned method has been well known as an optical emission actinometry(hereinafter referred to as "OEA").

The problem in measuring the radical distribution using the conventional OEA is explained in detail.

The radicals are excited by collision with the electrons in plasma to emit electromagnetic waves. At this time, the light intensity emitted from the radicals is not always proportional to the density of radicals, since the probability of the collision between the radicals and electrons is varied, as the energy distribution and density of electrons are changed. In this regard, the intensity of the light emitted from the radicals may be determined from the following equation (I) which is a function of the radical density and plasma parameters:

$$I_{Rad} \propto [Rad] n_e k_e \quad (I)$$

wherein, $I_{Rad}$ represents intensity of the light emitted from radicals;

[Rad] represents density of the radicals;

$n_e$ represents density of the plasma; and, $k_e$ is a coefficient depending upon the plasma parameters.

In the conventional OEA method, the radical distribution is measured by the following equation (II), in which proportional coefficient of the equation (I) is eliminated by employing the actinometer:

$$I_{Rad}/I_{Act} \propto [Rad]/[Act] \quad (II)$$

wherein, $I_{Act}$ represents intensity of the light emitted from actinometer; and,

[Act] represents density of the actinometer.

As described above, the OEA method measures the radical distribution using the light intensity ratio between the radicals and the actinometer, grounded on the fact that the actinometer, like the radicals, emits light by the collision of electrons, while it does not affect the discharge characteristics of the radicals. At this time, the collision probability of the actinometer and electrons should be same as that of the radicals and electrons, as the energy distribution and density of the electrons are changed.

In the conventional OEA method, a spatial distribution of the radicals is measured by employing the Abel's transformation. To measure the spatial distribution of the radicals through Abel's transformation, an apparatus for focusing light should be provided at the exterior of a vacuum container and the spatial light distribution is measured by applying the distribution angles of the light projected in this way to Abel's transformation, after all spatially distributed light is projected in any one direction. Accordingly, the OEA method essentially requires a large window positioned at the vacuum container.

However, it was very difficult to install such a large window on the conventional plasma apparatus. Moreover, it was impossible to measure any spatial distribution which is not in axial symmetry, since the Abel's transformation is built under the assumption that all spatially distributed light is in axial symmetry. Also, the conventional OEA method causes the plasma to be fluctuated due to the use of actinometer, errors in measurement are essentially accompanied, which is grounded on a fact that the spatial distribution of the actinometer is not uniform, and the errors become greater due to the secondary errors caused by the Abel's transformation.

SUMMARY OF THE INVENTION

The primary object of the present invention is, therefore, to provide a method for measuring distribution of radical species in plasma in more efficient and precise manner.

The other object of the invention is to provide a novel apparatus for measuring distribution of radical species in plasma.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

To accomplish the above object of the present invention, the method for measuring distribution of radical species in plasma comprises the steps of: (i) measuring the integral light intensity in a vacuum container with an optical probe inserted into the vacuum container; (ii) determining light intensity at each point of the vacuum container by differentiating the integral light intensity; (iii) measuring current and voltage applied to the electrostatic probe in the vacuum container; (iv) determining plasma parameters from the measured current and voltage; and, (v) measuring distribution of radical species from the light intensity and plasma parameters.

On the other hand, the apparatus for measuring distribution of radical species in plasma comprises: (i) a vacuum container; (ii) an optical probe having a colliminator, a first focusing lens, an insulated rod and an optical fiber, for measuring the light emitted from radical species in the vacuum container; (iii) an electrostatic probe made of a metallic rod covered with insulating material, for measuring current and voltage in the vacuum container; (iv) a linear motion means having a bellows tube, for carrying the optical probe and electrostatic probe into the vacuum container; (v) a light analyzing means having a second focusing lens, a spectroscope, a photosensor and a photosensor controller, for analyzing the light measured by the optical probe; (vi) an electric signal analyzing means having a detector for measuring current and voltage applied to the electrostatic probe and an analog to digital convertor for converting the analog signals transmitted from the detector to corresponding digital signals; and, (vii) a computing means for analyzing the distribution of radical species in the vacuum container based on the data transmitted from the light analyzing means and electric signal analyzing means, and controlling the moving direction and distance of the linear motion means and the sweeping of the electrostatic probe.

Hereinafter, a preferred embodiment of the present invention will be described in detail with reference to the accompanying drawings.

Figure 1:
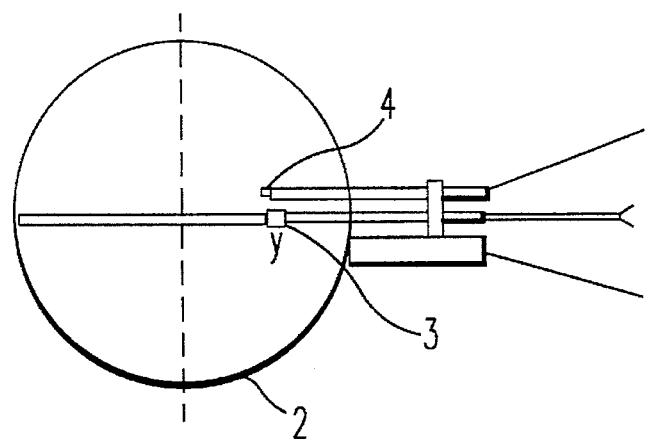
FIG. 1 is a schematic diagram showing a part of a measuring apparatus of the present invention.

As described above, the intensity of the light emitted from the radicals is conventionally determined from the equation (I). According to the present invention, the radical distribution is measured by directly determining the intensity of light emitted from the radicals, $n_e$ and $k_e$ in plasma. The light intensity may be measured by an optical probe(3) inserted to a vacuum container(2) as shown in FIG. 1, by employing the following equation (III).

$$I^{Int}(y) = \int I(x)dx \qquad (III)$$

wherein,

I(x) represents the light intensity at each point of the direction to which optical probe(3) is inserted; and, $I^{Int}(y)$ represents the integral light intensity from the left-side wall of vacuum container(2) to a position(y).

Since the amount of the light measured by the optical probe(3) is an integral, the light intensity I(x) at each point in the vacuum container(2) may be obtained by differentiating the measured integral light intensity($I^{Int}$) as in the following equation (IV).

$$I(x)=d[I^{Int}(y)]/dy|_{y=x} \qquad (IV)$$

Further, an electrostatic probe(4) is inserted to the vacuum container(2) to obtain $n_e$ and $k_e$, voltage is applied to the electrostatic probe(4), and then current flowing therethrough is measured. Then, I-V curve for the measured current(I) and applied voltage(V) is built, and $n_e$ and $k_e$ are obtained from the I-V curve. To sum up, the distribution of radicals in plasma may be determined, based on the light intensity measured by an optical probe(3) and the plasma parameters measured by an electrostatic probe(4).

Figure 2:
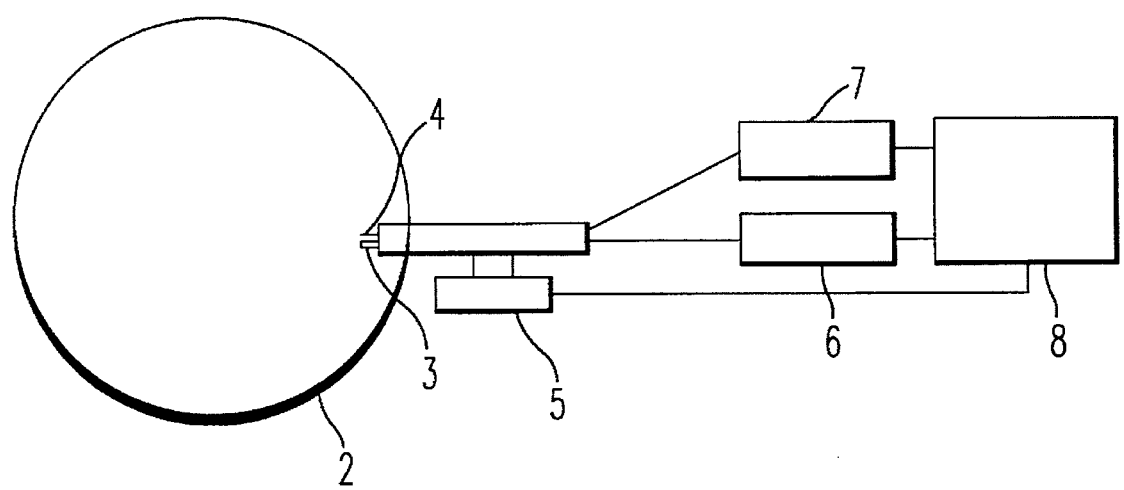
FIG. 2 is a block diagram illustrating a measuring apparatus of the invention.

FIG. 2 is a block diagram illustrating a measuring apparatus according to a preferred embodiment of the invention. As shown in FIG. 2, a hole is formed on the right-side wall of a vacuum container(2). A linear motion device(5), in which an optical probe(3) and an electrostatic probe(4) are mounted, is inserted into the vacuum container(2) through the hole. The optical probe(3) is designed to collect parallel light, and the collected light is transmitted to a spectrum analyzer(6) via an optical fiber provided in the optical probe(3). The spectrum analyzer(6) is made up of a second focusing lens, a spectroscope, a photosensor, and a photosensor controller. The second focusing lens collects the light emitted from the optical fiber provided in the optical probe (3) and transmits it to the spectroscope. The spectroscope separates the light according to its wavelength, and the light thus separated is detected by the photosensor connected to the photosensor controller. Then, the photosensor controller transmits the detected data to a computer.

On the other hand, an electric signal analyzer(7) is made up of a detector and A/D(analog to digital) convertor. The detector determines the current flowing into an electrostatic probe(4) and the voltage cross the electrostatic probe. The A/D convertor transforms the analog electric signal from the detector into a digital signal, and transmits it to a computer (8). The electric signal analyzer(7) sweeps the voltage cross the electrostatic probe(4) from +100 [V] to −100 [V], and the computer(8) controls the sweeping period and times. The linear motion device(5) also includes a bellows so that the optical probe(3) and the electrostatic probe(4) may linearly move in the vacuum container(2) to detect the light, current and voltage. The computer(8) also controls the moving direction and distance, and measures the spatial distribution of the radicals, based on the data transmitted from the spectrum analyzer(6) and the electric signal analyzer(7).

Figure 3:
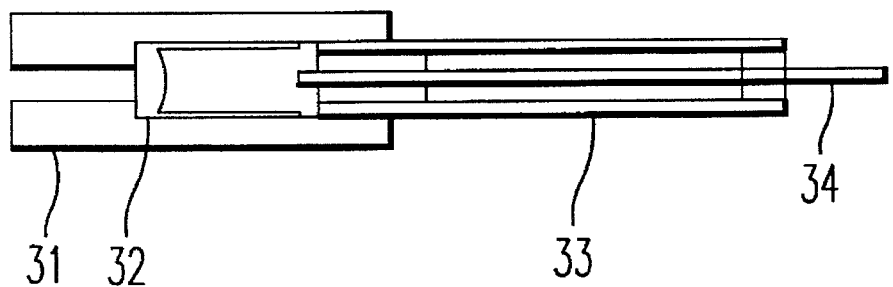
FIG. 3 is a partial view showing an optical probe of the measuring apparatus.

FIG. 3 is a partial view showing an optical probe of a measuring apparatus according to the invention. As shown in FIG. 3, a colliminator(31) is coupled to a first focusing lens(32), and the end of an optical fiber(34) is positioned within the focusing range of first focusing lens(32). The colliminator(31) is mounted to an optical probe(3) which only collects parallel incident light on the optical probe(3). Accordingly, only the light incident on the optical probe(3) in parallel, is transmitted to a spectrum analyzer(6) through the optial fiber(34). Moreover, an insulated rod(33) is mounted to a linear motion device(5) to prevent the optical fiber(34) from contacting with the plasma in a vacuum container(2).

Figure 4:
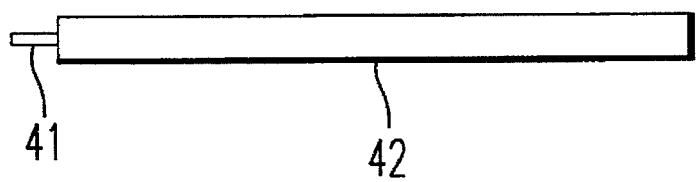
FIG. 4 is a partial view showing an electrostatic probe of the measuring apparatus; and, FIG. 5 is a partial view showing a linear motion means of the measuring apparatus.

FIG. 4 is a partial view showing an electrostatic probe of a measuring apparatus according to the invention. As shown in FIG. 4, an electrostatic probe(4) is made of a metal rod(41) of tungsten, platinum and the like, covered with insulating material.

Figure 5:
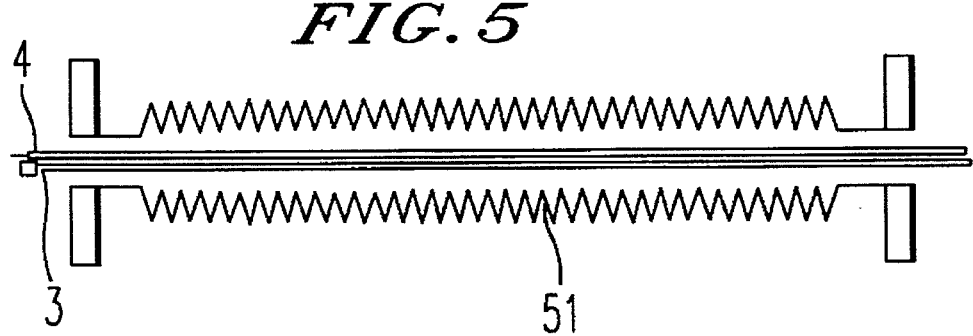

FIG. 5 is a partial view showing a linear motion means of a measuring apparatus according to the invention. As shown in FIG. 5, a linear motion device(5) has a bellows tube(51), which carries an optical probe(3) and an electrostatic probe (4) into a vacuum container(2). Accordingly, expansion and shrink of the bellows tube(51) makes the probes to move linearly.

As clearly illustrated above, the present invention provides a method for measuring radical species spatial distribution in plasma and an apparatus therefor by which the radical species spatial distribution can be measured in an efficient and precise manner.

What is claimed is:

1. A method for measuring distribution of radical species in plasma which comprises the steps of:
   (i) measuring the integral light intensity in a vacuum container with an optical probe inserted into the vacuum container;
   (ii) determining light intensity at each point of the vacuum container by differentiating the integral light intensity;
   (iii) measuring current and voltage applied to an electrostatic probe in the vacuum container;
   (iv) determining plasma parameters from the measured current and voltage; and,
   (v) measuring distribution of radical species from the light intensity and plasma parameters.

2. The method for measuring distribution of radical species in plasma of claim 1, wherein the integral light intensity in a vacuum container is obtained from the following equation (III):

$$I^{Int}(y) = \int^y I(x)dx \qquad (III)$$

wherein,

I(x) represents the light intensity at each point of the direction to which optical probe is inserted; and, $I^{Int}(y)$ represents the integral light intensity from the vacuum container to a current position of the optical probe in the vacuum container.

3. An apparatus for measuring distribution of radical species in plasma which comprises:
   (i) a vacuum container;
   (ii) an optical probe for measuring the light emitted from radical species in the vacuum container;
   (iii) an electrostatic probe for measuring current and voltage in the vacuum container;
   (iv) a linear motion means having a bellows tube, for carrying the optical probe and electrostatic probe into the vacuum container;
   (v) a light analyzing means for analyzing the light measured by the optical probe;
   (vi) an electric signal analyzing means having a detector for measuring current and voltage applied to the electrostatic probe and an analog to digital convertor for transforming the analog signals transmitted from the detectors to corresponding digital signals; and,
   (vii) a computing means for analyzing distribution of the radical species in the vacuum container based on the data transmitted from the light analyzing means and electric signal analyzing means, and controlling the moving direction and distance of the linear motion means and the sweeping of the electrostatic probe.

4. The apparatus for measuring distribution of radical species in plasma of claim 3, wherein the vacuum container has a hole for the insertion of a linear motion means.

5. The apparatus for measuring distribution of radical species in plasma of claim 3, wherein the optical probe has a colliminator, a first focusing lens, an insulated rod and an optical fiber.

6. The apparatus for measuring distribution of radical species in plasma of claim 3, wherein the electrostatic probe is made of a metal rod covered with insulating material.

7. The apparatus for measuring distribution of radical species in plasma of claim 3, wherein the light analyzing means has a second focusing lens, a spectroscope, a photosensor and a photosensor controller.

* * * * *